(12) United States Patent
Esformes et al.

(10) Patent No.: US 11,744,695 B2
(45) Date of Patent: Sep. 5, 2023

(54) SOFT TISSUE ATTACHMENT DEVICE

(71) Applicant: Howmedica Osteonics Corp., Mahwah, NJ (US)

(72) Inventors: Marc Esformes, Wappingers Falls, NY (US); Ellen Chan, Midland Park, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 256 days.

(21) Appl. No.: 16/372,993

(22) Filed: Apr. 2, 2019

(65) Prior Publication Data

US 2019/0307549 A1    Oct. 10, 2019

Related U.S. Application Data

(60) Provisional application No. 62/653,912, filed on Apr. 6, 2018.

(51) Int. Cl.
*A61F 2/08* (2006.01)
*A61F 2/00* (2006.01)
(Continued)

(52) U.S. Cl.
CPC .......... *A61F 2/0811* (2013.01); *A61F 2/0077* (2013.01); *A61F 2002/0081* (2013.01); *A61F 2002/0086* (2013.01); *A61F 2002/0817* (2013.01); *A61F 2002/0864* (2013.01); *A61F 2002/0888* (2013.01);
(Continued)

(58) Field of Classification Search
CPC ... A61B 17/064; A61B 17/0643; A61B 17/08; A61B 2017/0412; A61B 2017/0454; A61B 2017/0464; A61B 2017/0641; A61B 2017/0646; A61B 2017/081; A61F 2/0811; A61F 2/30771; A61F 2002/0077; A61F 2002/0086; A61F 2002/0823;
(Continued)

(56) References Cited

U.S. PATENT DOCUMENTS

| 5,632,748 A | * | 5/1997 | Beck, Jr ............... A61F 2/0811 |
| | | | 606/328 |
| 5,931,869 A | | 8/1999 | Boucher et al. |

(Continued)

FOREIGN PATENT DOCUMENTS

EP    2005975 A2    12/2008

OTHER PUBLICATIONS

Extended European Search Report including the Written Opinion for Application No. EP 19167488 dated Aug. 28, 2019, pp. 1-6.
(Continued)

*Primary Examiner* — Marcia L Watkins
(74) *Attorney, Agent, or Firm* — Lerner David LLP

(57) ABSTRACT

A device for attaching a soft tissue graft to bone includes a body with a smooth contoured first surface and a second surface opposite the first surface having a plurality of outwardly extending fixation members. The second surface is at least partially formed of a porous material adapted for bone ingrowth. A channel extends at least partially through the body in between the first and second surfaces for receiving a portion of the graft. The channel is at least partially formed of a porous material adapted for tissue ingrowth, bone ingrowth or a combination thereof.

13 Claims, 4 Drawing Sheets

(51) Int. Cl.
　　　*A61F 2/30*　　　(2006.01)
　　　*B33Y 80/00*　　　(2015.01)

(52) U.S. Cl.
　　　CPC ............ *A61F 2002/30761* (2013.01); *A61F 2220/0016* (2013.01); *A61F 2230/0006* (2013.01); *A61F 2230/0067* (2013.01); *A61F 2230/0069* (2013.01); *A61F 2230/0095* (2013.01); *A61F 2250/0024* (2013.01); *B33Y 80/00* (2014.12)

(58) Field of Classification Search
　　　CPC ...... A61F 2002/0829; A61F 2002/0847; A61F 2002/087; A61F 2002/0864
　　　See application file for complete search history.

(56) References Cited

U.S. PATENT DOCUMENTS

| | | | |
|---|---|---|---|
| 7,537,664 B2 | 5/2009 | O'Neill et al. | |
| 7,828,820 B2 * | 11/2010 | Stone | A61B 17/0401 606/232 |
| 7,942,914 B2 | 5/2011 | Cerundolo | |
| 8,147,546 B2 | 4/2012 | Stone et al. | |
| 8,496,657 B2 | 7/2013 | Bonutti et al. | |
| 8,728,387 B2 | 5/2014 | Jones et al. | |
| 8,858,634 B2 | 10/2014 | Lewallen | |
| 9,135,374 B2 | 9/2015 | Jones et al. | |
| 9,180,010 B2 | 11/2015 | Dong et al. | |
| 9,456,901 B2 | 10/2016 | Jones et al. | |
| 2005/0112397 A1 | 5/2005 | Rolfe et al. | |
| 2006/0241776 A1 | 10/2006 | Brown et al. | |
| 2007/0162022 A1 | 7/2007 | Zhang et al. | |
| 2010/0137996 A1 | 6/2010 | Clifford et al. | |
| 2013/0110183 A1 * | 5/2013 | Duggal | A61B 17/7064 606/328 |
| 2013/0131699 A1 | 5/2013 | Jiang et al. | |
| 2017/0156847 A1 * | 6/2017 | Ricci | A61F 2/0811 |
| 2017/0196678 A1 | 7/2017 | Park et al. | |

OTHER PUBLICATIONS

Reginald Lee et al., U.S. Appl. No. 62/517,456, filed Jun. 9, 2017, titled "Polymer Interlock Support Structure and Method of Manufacture Thereof".

* cited by examiner

SOFT TISSUE ATTACHMENT DEVICE

CROSS REFERENCE TO RELATED APPLICATIONS

The present application claims the benefit of the filing date of U.S. Provisional Patent Application No. 62/653,912 filed Apr. 6, 2018, the disclosure of which is hereby incorporated herein by reference.

BACKGROUND OF THE INVENTION

The present disclosure relates generally to orthopedic surgical implants and methods of use, and more particularly to devices for the attachment of soft tissue to bone.

Damaged soft tissue (for example, meniscus, cartilage, capsule, ligaments and tendons, replacement grafts of any of these soft tissues, or the like) may require replacement and/or reconstruction to reattach soft tissue to bone or replace the soft tissue with a soft tissue graft. For example, a typical surgical procedure for ligament replacement and reconstruction involves obtaining a tissue graft or a suitable synthetic graft to replace the damaged ligament. A graft may be either an autograft coming from another part of the patient's body, an allograft coming from a cadaver donor, or a synthetically manufactured material.

Generally, during ligament attachment surgery, a natural ligament or tendon or a synthetic graft is secured to a prepared bone. For example, in an anterior cruciate ligament (ACL) reconstruction procedure bone tunnels are formed through the patient's femur and tibia bones and a graft is implanted in the tunnels such that each end is secured to the tibia and femur, respectively, and the body of the graft spans the joint space between the bones.

Typically, the graft is secured within each tunnel using an implant to secure the ligament to the surrounding bone. For example, interference screws have been used to secure the graft within a tunnel by creating a tight interference fit between the graft and the bone of the wall surrounding the tunnel. However, direct contact of the graft with the threads of the interference screw at the healing site could damage the graft, or conversely, result in a less than optimal repair as the graft could slip past the interference screw. Alternatively, for example, a button anchor is used to secure a graft within a tunnel. The button anchor rests against the outer cortical surface of the bone and includes a loop of suture extending from the button anchor to the graft. The graft can be passed through the loop, and folded over itself, such that the graft is secured to the femur, and the two ends of the graft, extending from the suture loop and into the tibia, are secured to the tibia via another button anchor, an interference screw, or via another anchor as known in the art. Methods using the button anchor, however, must rely on the strength of the button anchor and suture, and in some instances, must rely on proper adjustment of the size of the suture loop to ensure appropriate positioning and tensioning of the graft.

Thus, there is a need in the art for improved soft tissue attachment devices that encourage stable and reliable fixation of the graft to the bone, can be implanted by easily repeatable procedures, and that maintain the integrity of the graft.

BRIEF SUMMARY OF THE INVENTION

According to an aspect of the present disclosure, a device for attaching a graft to bone includes a body having a smooth contoured first surface and a second surface opposite the first surface having a plurality of outwardly extending fixation members and at least partially formed of a porous material adapted for bone ingrowth. A channel extends at least partially through the body in between the first and second surfaces for receiving a portion of the graft. The channel is at least partially formed of a porous material adapted for tissue ingrowth, bone ingrowth or a combination thereof.

In other embodiments, the channel may be at least partially surrounded by an inner wall, at least a portion of the inner wall may be formed of the porous material. The fixation members may extend outwardly beyond the porous material. The fixation members may be formed of a solid material. The body in between the first and second surfaces may extend between a first lateral portion and a second lateral portion, and the channel may extend between the first lateral portion and the second lateral portion. The channel may include a first aperture and a second aperture and a saddle between the first and second apertures. The channel may be sized to accommodate at least two strands of the graft positioned through each of the first and second apertures and over the saddle. The saddle may be partially surrounded by the inner wall and may be co-extensive with the second lateral portion, at least a portion of the graft positioned on the saddle may be exposed at the second lateral portion of the body. The first and second apertures may be configured to return route of the graft through the channel.

According to another aspect of the present disclosure, a soft tissue attachment system for attaching a graft to bone includes an anchoring device having a body having a smooth contoured first surface, and a second surface opposite the first surface having a plurality of outwardly extending fixation members and at least partially formed of a porous material adapted for bone ingrowth. A channel extends at least partially through the body in between the first and second surfaces for receiving a portion of the graft. The channel is at least partially formed of a porous material adapted for tissue ingrowth, bone ingrowth or a combination thereof. A portion of the graft is disposed in a loop and positioned through at least a portion the channel.

In other embodiments, the channel may be at least partially surrounded by an inner wall, at least a portion of the inner wall may be formed of the porous material. The body in between the first and second surfaces extend may extend between a first lateral portion and a second lateral portion. The channel may extend between the first lateral portion and the second lateral portion. The channel may include a first aperture and a second aperture and a saddle between the first and second apertures. The channel may be sized to accommodate at least two strands of the graft positioned through each of the first and second apertures and over the saddle. The saddle may be partially surrounded by the inner wall and may be co-extensive with the second lateral portion, and at least a portion of the graft positioned on the saddle may be exposed at the second lateral portion of the body.

According to yet another aspect of the present disclosure, a method of attaching a graft having first and second ends to bone include forming a fixation area in a first bone; positioning the graft through a first opening, a channel, and first and second apertures, and around a saddle adjacent the first and second apertures of a soft tissue attachment device; positioning the device within the fixation area in the first bone; and securing the device at the fixation area by engaging a plurality of barbs extending outwardly from an outer surface of the device with the bone to fix the device in the bone. The channel and the outer surface are at least partially formed of a porous material adapted for tissue ingrowth, bone ingrowth or a combination thereof.

In other embodiments, the method may include securing a portion of the graft to a second bone. The soft tissue attachment device may include a saddle positioned in between the first aperture and the second aperture, and the step of positioning the graft may include, in order, positioning the graft through the first opening, through the channel, through the first aperture, over the saddle, through the second aperture, and back through the channel, and back through the first opening. The step of securing the device at the fixation area may include contacting the fixation area with the portion of the outer surface formed of the porous material, and the porous portion of the outer surface may be adapted for bone ingrowth. The step of forming the fixation area in the first bone may include forming a tunnel through the first bone adapted to accommodate at least a portion of the graft extending from the soft tissue attachment device.

DETAILED DESCRIPTION

Figure 1:
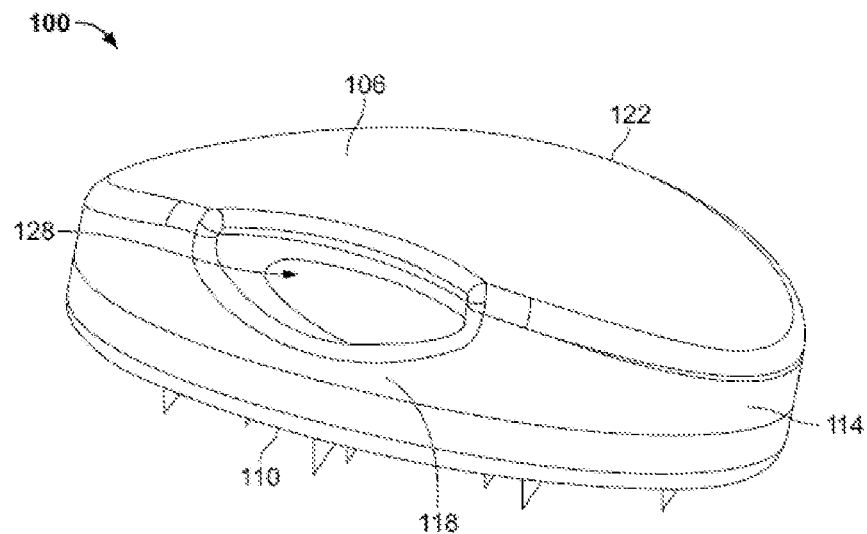
FIG. 1 shows a perspective top view of a soft tissue attachment device according to one embodiment of the present disclosure.

The following description of the embodiments of the disclosure are exemplary in nature and are in no way intended to limit the disclosure or its application or uses. As used herein, "soft tissue" may be, for example, meniscus, cartilage, ligaments and tendons, or the like, or artificial or natural grafts of any such tissues. Also as used herein, "tissue" will refer to soft tissue and "bone" will refer to bone, unless otherwise specified. While the present disclosure is described in the context of performing a procedure in the knee to reconstruct an ACL, it should be understood that aspects of the disclosure are not restricted to knee ligament reconstruction techniques. Instead, the aspects of the disclosure may be used in any suitable surgical procedure, which may be performed in any suitable body portion including other bone joints throughout the body. Moreover, the devices and methods disclosed herein may be used to secure other soft tissue including grafts, ligaments, tendons, etc. relative to other soft tissue and/or to one or more bones.

In one embodiment of the present disclosure, FIGS. 1-7 show soft tissue attachment anchoring device 100. Device 100 is produced through additive layer manufacturing (ALM), i.e. 3D printing, with portions of the device being porous, as will be discussed in further detail below.

Device 100 has a substantially circular shape, from a top view, although in other examples the device may be oval, triangular, rectangular, or any other shape. Device 100 includes first surface 106, second surface 110 opposite the first surface, and side wall 114 extending between the first and second surfaces and defining a width of the device. The edges between each of first and second surfaces 106, 110 with side wall 114 can be rounded.

Figure 2:
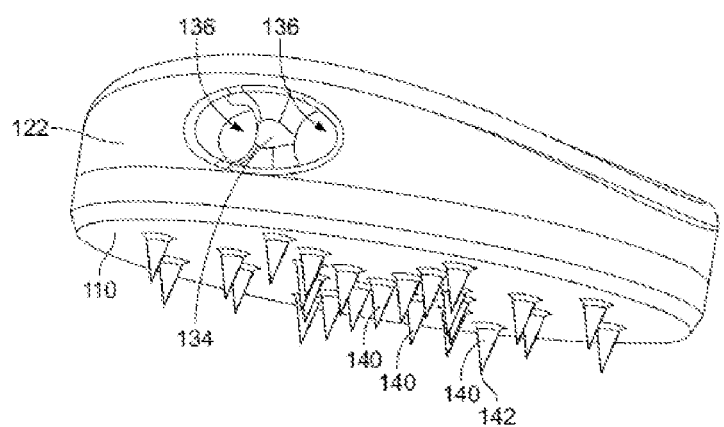
FIG. 2 shows a perspective bottom view of the device of FIG. 1.

As shown in FIGS. 1 and 2, first surface 106 is a polished, smooth contoured surface that is solid or substantially solid, i.e. not porous. First surface 106 is intended to be outward facing, once the second surface 110 is secured to bone, and thus the smooth surface may help to avoid irritation of the surrounding tissue. Second surface 110 is a roughened, porous surface, i.e. formed of a porous material, which facilitates tissue ingrowth into the device, for example, bone ingrowth. Second surface 110 includes a plurality of fixation members to aid in initial fixation of the device in the bone. In the illustrated embodiment, the fixation members are barbs or sharp pegs 140 positioned across second surface 110 and extending outwardly from the second surface. Each of the pegs 140 may be solid and conically shaped terminating at sharp point 142. Pegs 140 are positioned spaced apart along the second surface in a manner that allows the device to sit flush against the bone and prevents rocking of the device when the pegs are engaged with the bone. In other examples, the fixation member may be in any shape that helps provide initial fixation of the device at the second surface. For example, the fixation members may be in the shape of blades, knife-edge members, etc., or the fixation members may include one or more screws, fins, or the like, or other fixation features that can interlock with a shape of a prepared bone surface (dovetail feature, Morse taper, and the like).

FIGS. 1-3 and 5-7 illustrate a porous material formed along at least a portion of the surface area of the second surface 110. As illustrated, in this embodiment, the pegs 140 may extend beyond the porous material such that the pegs 140 can create the initial fixation to the bone. As discussed further below, with the pegs engaged with the bone and with the porous material compressed against the bone surface (which is typically prepared by, for example, removal of the cortical layer), bone ingrowth may take place to integrate bone tissue into the porous material which may result in a secondary fixation between the implant and the bone. The porous material may have any thickness desired, such as, for example, between about 0.5 to 2.5 millimeters. Additionally, the thickness of the porous material may vary along the implant or it may be constant.

Continuing with this embodiment, the side wall 114 of device 100 forms a lateral wall of device 100, along which a first lateral portion 118 and a second lateral portion 122 opposite the first portion and spaced apart from one another about 180 degrees on the device. First portion 118 includes opening or aperture 128 extending through side wall 114 that leads into channel 130 within the body of the device 100. Aperture 128 is generally oval shaped and defines a length that is transverse to the width of the device. Aperture 128 may be positioned on side wall 114 closer to first surface 106 than to second surface 110. Although in alternative embodiments, the aperture may be circular or any other shape and may be positioned anywhere on side wall 114, or alternatively, all or a portion of the aperture may be positioned on first surface 106.

Figure 3:
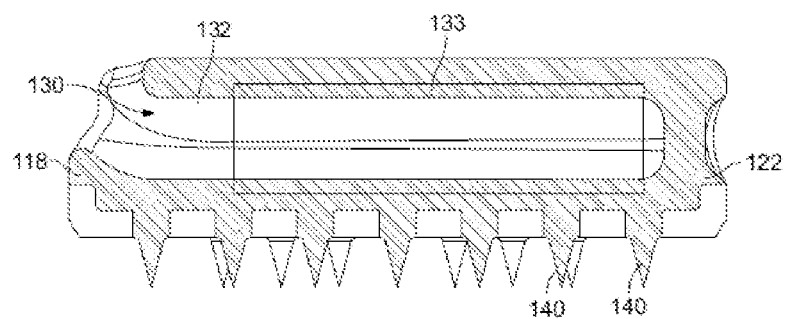
FIG. 3 shows a cross-sectional side view of the device of FIG. 1.
Figure 4:
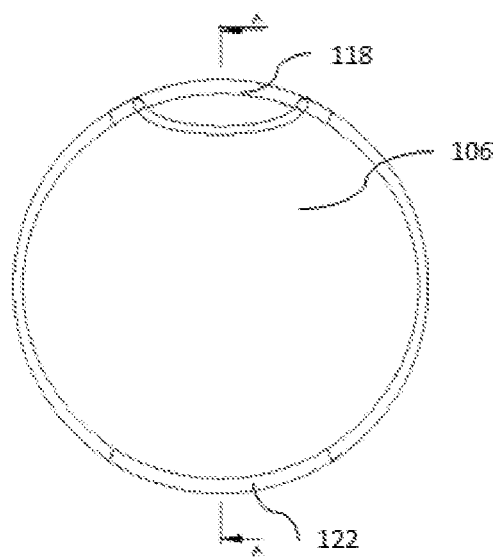
FIG. 4 is a top view of the device of FIG. 1.
Figure 5:
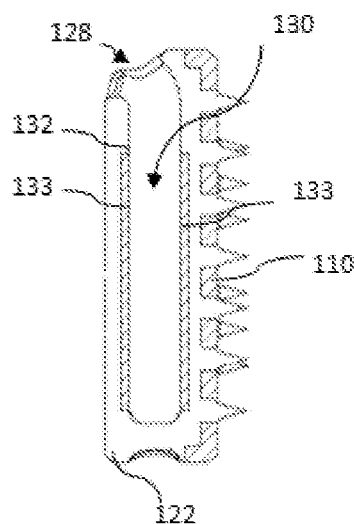
FIG. 5 is a cross-sectional view taken along the line A-A in FIG. 4.
Figure 7:
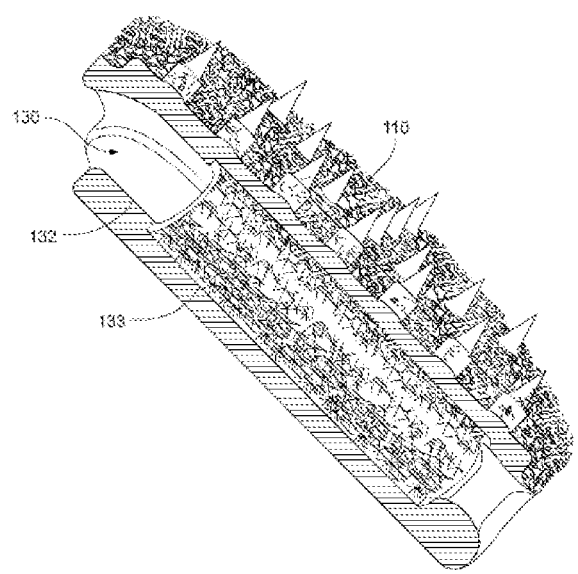
FIG. 7 shows a cross-sectional side view of the device of FIG. 1 with tissue-ingrowth material details on certain surfaces of the device.

As shown in FIGS. 3, 5 and 7, aperture 128 leads into enclosed channel 130 and forms a first end of the channel at first portion 118. Channel 130 extends through the body of device 100 to a second end that terminates at saddle 134 at second portion 122. Channel 130 is sized and shaped for receiving at least two strands of a graft within the body of the device. Channel 130 is surrounded by inner wall 132 and may have a generally cylindrical shape. At least a portion 133 of inner wall 132, shown in FIGS. 3 and 5 as the general area identified as 133, is porous, i.e. formed of a porous material, while any remaining portion of the inner wall 132 is solid or substantially solid. The porous surface of inner wall 132 enables ingrowth of tissue into the inner wall, for example, bone ingrowth, soft tissue ingrowth, or a combination of bone and soft tissue ingrowth. Alternatively, the entirety of the inner wall may be porous.

Figure 6:
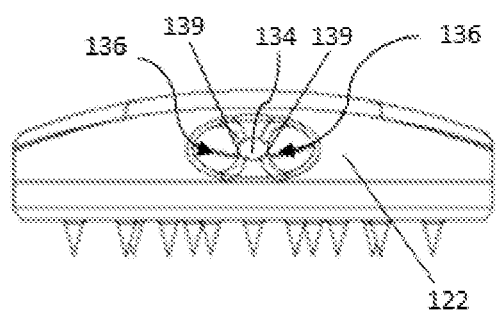
FIG. 6 is a front view of the device of FIG. 1.

Channel 130 terminates at saddle 134, which may be any feature that allows positioning of the graft or any other structure within the channel such that is passes through aperture 128 and forms a loop around saddle 134 such that the graft wraps around the saddle and extends through the channel in a direction back toward aperture 128—i.e., the graft folds over itself within channel 130. In this manner, saddle 134 is configured to return route the graft. In the illustrated embodiment, as shown in FIGS. 2 and 6, the saddle 134 is positioned between a pair of apertures 136 having perimeters enclosed within the side wall 114 at second portion 122. Apertures 136 are adjacent to one another and are separated by saddle 134. Saddle 134 has opposing concave surfaces 139 to help prevent damage to the graft extending through the apertures, particularly upon tensioning of the graft which may cause the graft to be constrained by saddle 134 and compressed against the saddle. Apertures 136 are each sized and shaped to allow at least one strand of a graft to pass through the aperture, and may be sized to allow additional strands of graft to pass through. Although in other embodiments, the apertures may instead be openings having any shape, such as slots. In this manner, channel 130 may constitute two separate apertures 136 which extend through the body as separate throughbores, or alternatively, apertures 136 may open into a common channel 130 within the body of device 100, such that the graft folded upon itself can remain in fluid contact with one another directly within channel 130. The latter may allow for increased tissue ingrowth into the porous material.

As discussed below, the graft may be passed through device 100 either by passing one or more ends of the graft into the first portion 118, through channel 130 and out second portion 122 through one aperture 136, where the one or more ends would then be passed over saddle 134 and into the other aperture 136, through channel 130 and back out first portion 118. Alternatively, one or more of the ends of the graft could be passed through the second portion 122 and into one of the apertures 136, through channel 130, and out the first portion 118, while the other of the end or ends could be passed through second portion 122 and into the other aperture 136, through channel 130, and out the first portion 118, such that the graft is again positioned around saddle 134 at the second portion 122.

In the illustrated embodiment, saddle 134 extends the entire thickness of side wall 114 and is substantially flush with side wall 114. Alternatively, saddle 134 may have a thickness that is thinner than the side wall 114 such that the saddle 134 is recessed from the side wall rather than being flush. In another alternative, the saddle 134 could be positioned elsewhere within the device 100, even closer to aperture 128 of the first portion 118.

To use the soft tissue attachment device 100 of the present disclosure, in one exemplary embodiment, such a method would include the operator first preparing the bone surface for positioning of the device 100 thereon. Typically, this may involve removing the cortical layer such that the porous portion of the second surface 110 contacts the underlying cancellous bone to promote tissue ingrowth. Next, optionally for tissue repair such as ACL reconstruction, the operator next drills the typical bore or tunnel in a bone forming the joint for receiving the soft tissue or replacement tendon or ligament. In the case of ACL reconstruction, a bone tunnel for receiving the replacement ligament is prepared in the tibia and the femur, and the surgeon creates a fixation area in a first bone (typically the femur but could be the tibia, or both) for device 100 to sit flush with the existing bone.

A first end (or bundled ends) of a graft (natural or synthetic) is inserted through aperture 128 at first portion 118 and into channel 130 of device 100, while the second end (or bundled ends) of the graft is positioned outside of the device. The first end of the graft then extends to the second portion 122 and through a first aperture 136 such that the end of the graft is positioned outside of side wall 114 of the device and is looped around saddle 134 and enters the second aperture 136 to re-enter channel 130. The first end of the graft then extends back through the channel in a direction toward first portion 118 and out of aperture 128 and out of the body of the device.

Alternatively, to position the graft, having first and second free ends, within channel 130, each of the free ends may be positioned in one of the apertures 136 and pulled toward and out of opening 128 such that the graft comes to rest folded over itself and positioned on saddle 134.

In either case, a portion of the graft is enclosed within the channel 130, and positioned against the porous portion therein, a portion is exposed adjacent saddle 134, and another portion is external to the channel extending from first portion 118. Thus, in this example, two strands of the same graft are positioned into the channel 130 to engage the graft to the device. The device 100 may have a friction-engaging feature within channel 130 to provide initial securement between the device 100 and the graft. Such features may include a tapered or wedge feature, a cleat, a channel 130 having a constricting size to impart friction along the graft positioned therein, or the like. Apertures 136 adjacent saddle 134 also provide additional surface area contact between device 100 and the graft as the graft is limited in its mobility due to the compression of the graft against saddle 134, particularly once tension is applied to the graft.

With the two free ends of the graft extending external to device 100, the device is inserted adjacent to or within the first bone tunnel and positioned at the prepared fixation area. Pegs 140 are driven into the bone to provide initial fixation of device 100 to the first bone. Second surface 110 may sit flush on the bone, or otherwise form a consistent surface with the surrounding bone to minimize irritation to the surrounding tissue, after the pegs are driven into and engaged with the bone. If present, a screw or other fixation member would also be engaged with the bone at this time. The two free ends are then secured to a second bone with another implant, whether a second device or other implant such as an interference device. In the case of ACL reconstruction, device 100 may be positioned and secured at a fixation area in the femur, and the free ends secured to the tibia, or vice versa.

FIG. 5 shows the portions of device 100 that are porous, which are marked in the figure with hatching. Thus, as described above and as shown in FIG. 5, second surface 110 and portion 133 of the inner wall 132 are porous. Second surface 110 being porous promotes subsequent bone ingrowth into device 100, allowing for better fixation of the device within the patient over time and allows for quicker healing. Portion 133 of inner wall 132 being porous likewise enables bone ingrowth, tissue ingrowth, or a combination of thereof, which enables seamless and robust attachment of the tissue to bone. Additionally, the bone ingrowth may provide for vascularization to occur from bone to tissue. To this end, these two porous portions may be adjacent to or even in contact with one another to help ensure robust ingrowth throughout the device and onto the graft. FIG. 7 illustrates a detailed representation of device 100 with ingrowth shown within channel 130 and on second surface 110. This ingrowth establishes fixation between device 100 and the bone adding stability to the device, which promotes robust attachment of the graft with the bone.

Optionally, device 100 may include a removable shuttle element, such as wire or suture, extending through the device along the route that the graft is intended to take which may simplify insertion of the graft within the channel 130. The shuttle element may have two ends, a first end having a tab for an operator to grasp and pull during placement of the graft within the device and a second end for engaging with the graft. In this example, the shuttle element may be positioned to form a loop through the channel 130 and around saddle 134. In the final configuration, in which the operator receives it, the two ends of the graft can be positioned outside aperture 128 of first portion 118.

Alternatively, the shuttle element may extend between two ends, and each end is adapted for engaging an end of the graft. The shuttle element may also include a tab for the operator to pull that may be positioned at a location between the two ends of the shuttle element. In the final configuration, the tab can be positioned outside and adjacent to aperture 128 of first portion 118 and each of the ends is positioned through one of the apertures 136 of second portion 122.

In either exemplary configuration, the end or ends engage the graft and the operator pulls the shuttle to thread the graft into the device 100. Other shuttle configurations are also envisioned which may be suitable for simplified positioning of the graft into the device 100.

As such, the present disclosure may also include various systems and kits based on the devices discussed above. For example, kits of the present disclosure may include at least one device 100 with a shuttle configured within the device, as described above. The kit may optionally include the graft. Further, the kit may optionally include additional implants, such as another device 100, an interference device, a button anchor, or the like, for securing the graft at a second location. The kit may be included in a single package or in separate packaging which are later brought together as a kit.

In another embodiment, the bone tendon attachment device can be of another shape than those illustrated. For example, the device may have a tapered shape which could, instead of being positioned on the surface of the bone, could be driven into the bone to secure itself to the bone. As discussed above, at least a portion of the outer surface may include bone engagement features such as spikes. Further, the device may include one or more through holes for inserting screws to further secure the device to bone. The device may be completely driven into the bone or partially. For example, a proximal portion of the device may include an opening through which tissue may be placed, and this proximal opening may remain outside of the bone such that the tissue can be secured thereto (e.g., whether by looping the graft through the opening or by securing suture between the proximal opening and the tissue.

Alternatively or additionally, the tissue may be secured by one or more sutures at a distal end, opposite the proximal opening, of the device. For example, a portion of the device may be formed of mesh, or other porous material, through which a suture can be passed. Further, a portion of the outer surface and/or a portion of the inner surface may include a porous ingrowth surface, such as that described above in reference to device 100, to allow for tissue and/or bone ingrowth as discussed above.

Continuing with this embodiment, in use, the device could be driven directly into bone or, for example, a slot may be created in the bone at an angle such that the slot is not oriented perpendicular to the bone. The device may be inserted in the slot so that the device is at a non-right angle with the bone to achieve sufficient fixation, as would a tent stake or the like.

In one embodiment, the devices disclosed herein are monolithic and are formed layer-by-layer using an additive layer manufacturing (ALM), i.e., 3D printing, process so no separate connection mechanism is necessary to bring together any of the components of the implant. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901, the disclosures of which are hereby incorporated by reference in their entireties herein. Assembly of a device in whole or in part using ALM is discussed in greater detail below.

In some arrangements, the device is formed using an ALM fabrication process, such as SLS, SLM or EBM described above, fused deposition modeling (FDM), or other appropriate 3D printing technologies known to those skilled in the art. When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the implant including the porous layers. In some instances, materials for one layer may be different than the materials for successive layers.

To form the porous layer in particular, porous geometries may be digitally modeled using cells as described in U.S. Pat. Nos. 9,180,010 and 9,135,374, the disclosures of which are hereby incorporated by reference in their entireties herein. A first layer or portion of a layer of powder is deposited and then scanned with a high energy beam to create a portion of a plurality of predetermined porous geometries. Successive layers of powder are then deposited onto previous layers of the powder and then scanned with the high energy beam. The scanning and depositing of successive layers of the powder continues the building process of the predetermined porous geometries. The porous geometries of the formed porous layers may define pores that may be interconnecting to provide an interconnected porosity. Further details regarding this high energy beam ALM process are described in U.S. Prov. Pat. App. No. 62/517,456, hereby incorporated by reference herein in its entirety.

Materials used to form the devices described above with an ALM process include, but are not limited to, metals (e.g., metal powder) that may be any one or any combination of titanium and its alloys (such as a porous titanium alloy, including Tritanium® by Howmedica Osteonics Corporation), stainless steel, magnesium and its alloys, cobalt and its alloys including cobalt chromium alloys, nickel and its alloys, platinum, silver, tantalum niobium, and other super elastic materials such as copper-aluminum alloys. Non-metallic materials may also be used and include, but are not limited to, implantable plastics. These may be any one of or a combination of wax, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials such as collagen/cell matrices.

The porous portions may also be seeded with various tissue ingrowth promoters, including for example hydroxyapatite, tricalcium phosphate, collagen-based additives, platelet-rich plasma, bioactive glass, or the like.

In one embodiment, a device for attaching a graft to bone comprising, a body having a smooth contoured first surface, a second surface opposite the first surface having a plurality of outwardly extending fixation members and at least partially formed of a porous material adapted for bone ingrowth, and a channel extending at least partially through the body in between the first and second surfaces for receiving a portion of the graft, wherein the channel is at least partially formed of a porous material adapted for tissue ingrowth, bone ingrowth or a combination thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for attaching a graft to bone comprising:
a body having a smooth contoured first surface, a second surface opposite the first surface having a plurality of outwardly extending fixation members and at least partially formed of a first porous material adapted for tissue ingrowth, each fixation member extending monolithically from the second surface and defining a distal end configured to engage bone, and a channel extending through the body in between the first and second surfaces for receiving a portion of the graft, wherein the body in between the first and second surfaces extends between a first lateral portion and an opposite second lateral portion, the channel extending from a first opening on the first lateral portion to a second opening on the second lateral portion, the first opening including first and second apertures, wherein the channel is defined by and surrounded by first, second and third inner walls, the first and second inner walls formed of a solid material and the third inner wall formed of a second porous material adapted for tissue ingrowth, the third inner wall disposed between the first and second inner walls of the channel, the first inner wall extending from the first lateral portion to the third inner wall and the second inner wall extending from the second lateral portion to the third inner wall.

2. The device of claim 1, wherein the first inner wall defines a first length and the second inner wall defines a second length, the first length being different from the second length.

3. The device of claim 1, wherein the fixation members extend outwardly beyond the first porous material.

4. The device of claim 3, wherein the fixation members are formed of a solid material.

5. The device of claim 2, wherein the channel includes a saddle between the first and second apertures.

6. The device of claim 5, wherein the channel is sized to accommodate at least two strands of the graft positioned through each of the first and second apertures and over the saddle.

7. The device of claim 5, wherein the saddle may be partially surrounded by the second inner wall and is co-extensive with the second lateral portion such that at least a portion of the graft positioned on the saddle is exposed at the second lateral portion of the body.

8. The device of claim 5, wherein the first and second apertures are configured to return route of the graft through the channel.

9. A soft tissue attachment system comprising:
an anchoring device having a body having a smooth contoured first surface, a second surface opposite the first surface having a plurality of outwardly extending fixation members and at least partially formed of a first porous material adapted for tissue ingrowth, each fixation member extending monolithically from the second surface and defining a distal end configured to engage bone, and a channel extending through the body in between the first and second surfaces for receiving a portion of a graft, wherein the body in between the first and second surfaces extends between a first lateral portion and an opposite second lateral portion, the channel extending from a first opening on the first lateral portion to a second opening on the second lateral portion, the first opening including first and second apertures, wherein the channel is defined by and surrounded by first second and third inner walls, the first and second inner walls formed of a solid material and the third inner wall formed of a second porous material adapted for tissue ingrowth, the third inner wall disposed between the first and second inner walls of the channel, the first inner wall extending from the first lateral portion to the third inner wall and the second inner wall extending from the second lateral portion to the third inner wall; and
a graft, wherein a portion of the graft is disposed in a loop and positioned through at least a portion of the channel.

10. The system of claim 9, wherein the first inner wall defines a first length and the second inner wall defines a second length, the first length being greater than the second length.

11. The system of claim 10, wherein the channel includes a-a saddle between the first and second apertures.

12. The system of claim 11, wherein the channel is sized to accommodate at least two strands of the graft positioned through each of the first and second apertures and over the saddle.

13. The system of claim 11, wherein the saddle is partially surrounded by the second inner wall and is co-extensive with the second lateral portion, wherein at least a portion of the graft positioned on the saddle is exposed at the second lateral portion of the body.

* * * * *